United States Patent
Bliss et al.

(10) Patent No.: US 6,289,890 B1
(45) Date of Patent: Sep. 18, 2001

(54) PORTABLE RESCUE BREATHING DEVICE

(75) Inventors: Peter L. Bliss, Prior Lake; Robert W. McCoy, Apple Valley, both of MN (US)

(73) Assignee: Valley Inspired Products, LLC, Burnsville, MN (US)

( * ) Notice: Subject to any disclaimer, the term of this patent is extended or adjusted under 35 U.S.C. 154(b) by 0 days.

(21) Appl. No.: 09/045,424

(22) Filed: Mar. 20, 1998

(51) Int. Cl.[7] .................................................. A61M 16/00
(52) U.S. Cl. ............................ 128/203.11; 128/204.21; 128/205.23
(58) Field of Search ..................... 128/202.28, 202.29, 128/203.11, 204.21, 205.23; 601/41–44

(56) References Cited

U.S. PATENT DOCUMENTS

| | | | |
|---|---|---|---|
| Re. 34,800 | 11/1994 | Hutchins | 128/898 |
| 1,848,232 | * 3/1932 | Swope et al. | 128/205.23 |
| 2,408,136 | * 9/1946 | Fox | 128/205.23 |
| 3,613,677 | * 10/1971 | Blasko | 128/204.21 |
| 3,874,378 | * 4/1975 | Isaacson et al. | 128/205.23 |
| 4,196,725 | * 4/1980 | Gunderson | 128/205.25 |
| 4,244,361 | * 1/1981 | Neubert | 128/204.21 |
| 4,297,999 | * 11/1981 | Kitrell | 128/205.23 |
| 4,340,045 | 7/1982 | Manley | 128/204.24 |
| 4,500,971 | 2/1985 | Futaki et al. | 704/274 |
| 4,588,383 | 5/1986 | Parker et al. | 434/265 |
| 4,711,585 | * 12/1987 | Fresquez et al. | 601/41 |
| 4,766,894 | 8/1988 | Legrand et al. | 128/204.21 |
| 4,863,385 | 9/1989 | Pierce | 434/265 |
| 4,898,174 | 2/1990 | Fangrow, Jr. | 128/204.24 |
| 4,932,879 | * 6/1990 | Ingenito et al. | 601/41 |
| 5,188,098 | * 2/1993 | Hoffman et al. | 128/204.21 |
| 5,239,988 | * 8/1993 | Swanson et al. | 601/41 |
| 5,271,389 | 12/1993 | Isaza et al. | 128/204.21 |
| 5,303,699 | 4/1994 | Bonassa et al. | 128/204.21 |
| 5,327,887 | * 7/1994 | Nowakowski | 128/204.21 |
| 5,377,671 | 1/1995 | Biondi et al. | 128/204.23 |
| 5,394,892 | * 3/1995 | Kenny et al. | 601/41 |
| 5,398,676 | 3/1995 | Press et al. | 128/204.23 |
| 5,496,257 | * 3/1996 | Kelly | 601/41 |
| 5,596,984 | 1/1997 | O'Mahony et al. | 128/205.24 |
| 5,662,099 | 9/1997 | Tobia et al. | 128/205.15 |
| 5,711,295 | * 1/1998 | Harris, II | 128/202.28 |
| 5,752,509 | * 5/1998 | Lachmann et al. | 128/204.21 |
| 5,806,512 | * 9/1998 | Abramov et al. | 128/204.21 |
| 6,024,089 | * 2/2000 | Wallace et al. | 128/204.21 |

* cited by examiner

Primary Examiner—Aaron J. Lewis
(74) Attorney, Agent, or Firm—Nikolai & Mersereau, P.A.

(57) ABSTRACT

A portable rescue breathing device provides people with minimal training with the ability to assist victims who are breathing inadequately or not at all. The portable rescue breathing device provides a pressurized source of air at a controlled and varying rate. The portable breathing device also provides voice instructions to people using the device to assist a victim and monitors pressure to provide diagnostic data.

28 Claims, 2 Drawing Sheets

PORTABLE RESCUE BREATHING DEVICE

BACKGROUND OF THE INVENTION

I. Field of the Invention

This invention relates generally to respiration assist devices. More particularly, this invention relates to a portable device which can be used by people with minimal training to provide emergency assistance to victims having trouble breathing or who have ceased breathing.

II. Discussion of the Prior Art

Various respirators and ventilators have been designed to assist patients with their breathing. These devices are generally designed to inject breathable gases (air) into a patient's lungs at a controlled rate and pressure. The operation of such prior art devices requires significant training given the dangers that can arise from improper use. Problems can arise if gases are delivered at an improper rate or pressure. If too little gas is delivered, the air supply will be inadequate to provide proper assistance to the patient. Delivery of the gas at too high a pressure can cause gastric insufflation (air in the stomach), which is a major cause of vomiting. Aspiration of material vomited into the mask of a respirator or ventilator can cause serious lung trauma. Delivery of the gas at too high a pressure can also cause lung trauma directly.

Proper parameters for delivery of gases will differ depending upon the size, weight and age of the victim. Proper settings of tidal volume, minute volume, frequency, pressure maximums and peak flow all can vary from patient to patient.

In emergency situations there is not often someone present who has the skills and training necessary to properly assess the situation and operate a standard ventilator or respirator for the maximum benefit of the patient. Yet, in such emergency situations, the need to provide assistance can be immediate. Also, in emergency situations even those trained in cardiopulmonary resuscitation have difficulty administering mouth-to-mouth, mouth-to-mask or even bag-valve-mask resuscitation. Therefore, it would be desirable to provide an easy-to-operate breathing assist device that can be operated with minimal training for the maximum benefit of the person in crisis. The present invention is designed to meet this need.

SUMMARY OF THE INVENTION

The portable breathing assist device of the present invention consists of:

(1) a gas source;
(2) a pressure sensor to monitor the pressure being imposed on the victim;
(3) a first valve which directs air into the patient on inhalation and out to the atmosphere on exhalation;
(4) a second valve for venting pressure out of the device on exhalation;
(5) tubing and a mask to direct air into the victim's mouth, nose, or mouth and nose;
(6) a microprocessor-based control module;
(7) a voice prompt module; and
(8) various input switches.

The gas source may be of several designs. It may be an air pump driven by an electric motor. It may be reciprocating air pump driven by a linear electromagnet (solenoid). It may be a container pressurized with air or oxygen delivered through a pressure reducing regulator and valve actuatable by a solenoid.

The pressure sensor, typically a pressure transducer, is positioned in the circuit between the gas source and the face mask. The pressure sensor delivers electrical signals proportional to the pressure to a microprocessor-based control module. The first valve is connected directly to the mask which is positioned over the victim's face.

The microprocessor-based controller operates the device in accordance with a pre-existing set of instructions. This set of instructions causes the microprocessor to respond in an appropriate fashion to inputs it receives from the pressure sensor and the various operator switches. The controller's responses include outputs to the gas source (proportional valve, motor or solenoid) and the voice module. Thus, the controller not only controls the delivery of air to the victim, but also provides voice instructions to the user related to the patient's needs and the operation of the breathing assist device.

The various aspects and advantages of the present invention will become clear from reading the following detailed description of the preferred embodiment in conjunction with the drawings which are also a part of this disclosure.

DETAILED DESCRIPTION OF THE PREFERRED EMBODIMENT

Figure 1:
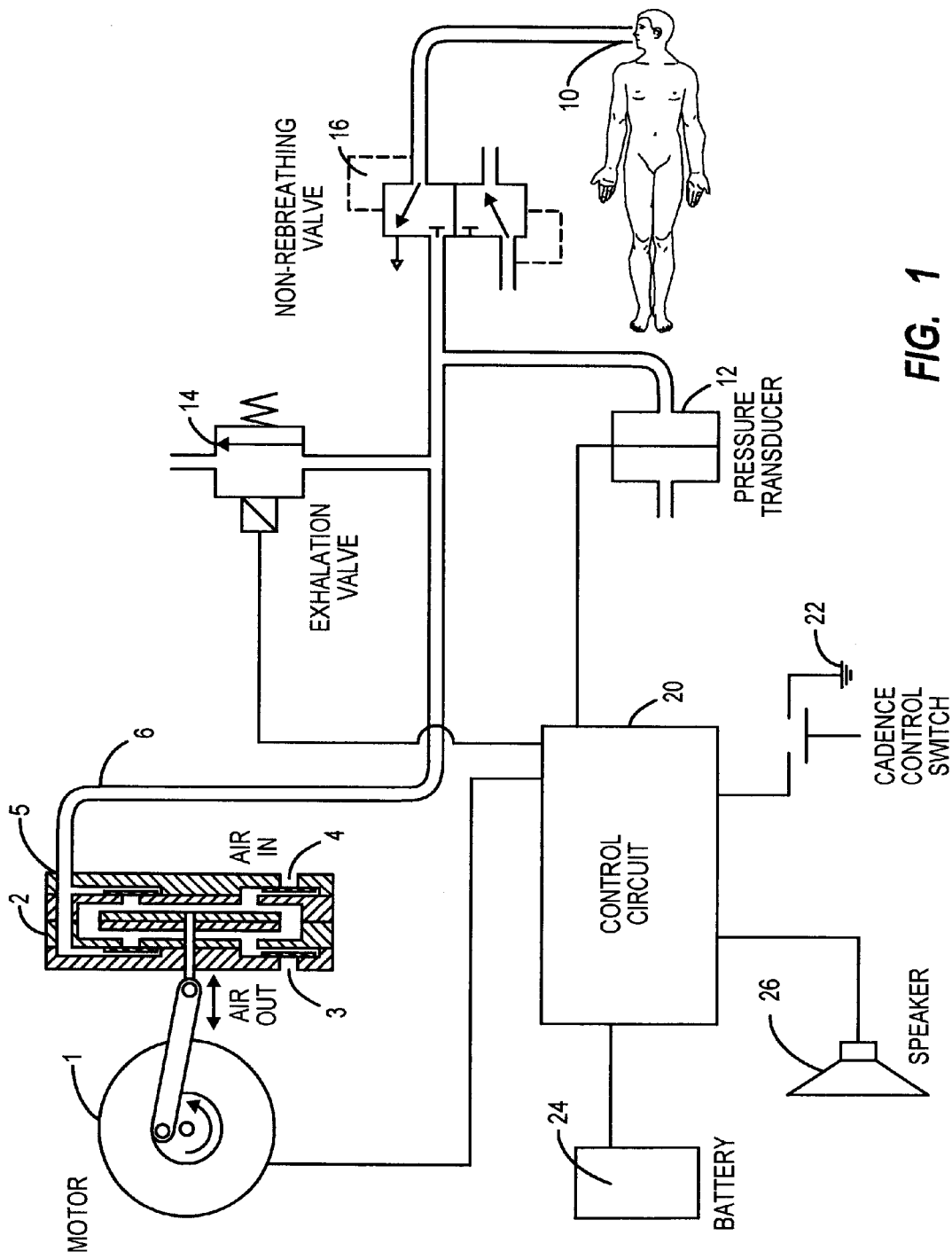
FIG. 1 is a schematic diagram of a first embodiment of the present invention.

FIG. 1 shows one embodiment of the present invention. Shown is a motor 1 for driving a pump 2. Alternatively, the motor can be replaced by an electromagnetic solenoid which drives the pump. The pump has a pair of air inputs 3 and 4 and an air output 5 coupled to one end 7 of a tube 6. The opposite end of the tube 6 is coupled to a face mask 10. Coupled to tube 6 intermediate the pump 2 and the mask 10 are a pressure sensor 12 in the form of a pressure transducer, an exhalation valve 14 for venting pressure out of the device on exhalation, and a non-breathing valve 16 which directs air into the patient on inhalation and out to the atmosphere on exhalation.

A key component of the device is the microprocessor-based controller 20. Controller 20 will typically include a microprocessor, read-only memory (ROM) or electrically programmable read-only memory (EPROM) for storing program instructions, and random access memory (RAM) for temporary storage of data. Controller 20 is electrically coupled to various operator switches, such as a cadence control switch 22. Controller 20 is also electrically coupled to the pressure sensor 12, the actuator for exhalation valve 14, and the motor 1. The two remaining components shown in FIG. 1 are the battery 24 that powers the device and a speaker 26 that is also electrically coupled to a voice module of the controller 20. By this arrangement, treatment can be delivered in a controlled fashion to the patient based upon the program. The inputs the controller receives from the switches (such as 22) and the sensor 12 are processed by the controller so that the controller can output control signals so the motor 1 and exhalation valve 14. Signals also are processed so that the voice module of controller 20 can deliver voice synthesized instructions to the user via speaker 26.

Figure 2:
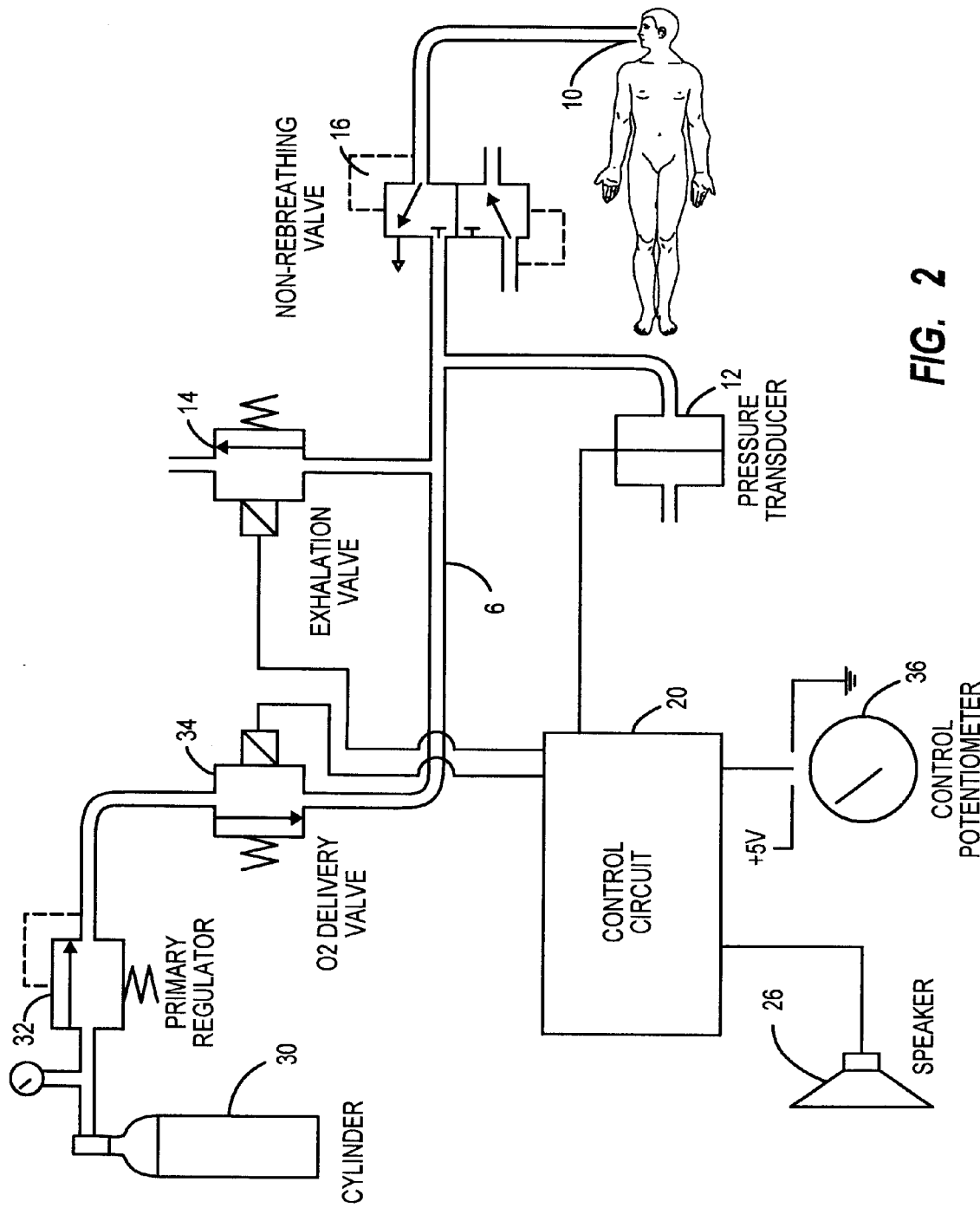
FIG. 2 is a schematic diagram of a second embodiment of the present invention.

The apparatus shown in FIG. 2 is practically identical to the apparatus of FIG. 1. The only difference is that FIG. 1's motor and pump 2 have been replaced by a cylinder 30 containing pressurized air or oxygen, a primary regulator 32 and a delivery valve 34. The controller 20 is electrically coupled to the delivery valve 34 and is, therefore, able to provide control signals to delivery valve 34. Also, FIG. 2 shows a potentiometer 36 coupled to the controller 20 as one of the switches.

The apparatus of the present invention has various modes of operation. On start-up, the controller 20 causes the speaker 26 to deliver instructions to the user to (a) call 911; (b) check the victim's airway for obstructions; (c) place the mask over the victim's face; and (d) pull the victim's jaw forward to open the airway. The device then waits for five seconds to see if it detects an inspiratory effort during this time period. Specifically, the controller 20 watches for signals representative of a decrease in pressure measured by the pressure sensor 12. If such an effort is detected, the device enters a spontaneous breathing mode. Otherwise, the device enters a mandatory mode.

The spontaneous mode allows the victim to breath naturally. The device monitors the volume of air inhaled. If this volume is below a predetermined minimum level, the apparatus increases the pressure it delivers during inhalation to assist the victim's inspiratory effort. This increased pressure level will force a greater volume of gas into the lungs to supplement the victims own breathing.

While in the spontaneous mode, the controller continually monitors the time between breaths. If no breath is detected during a predetermined time period, the device switches to the mandatory mode.

When the apparatus of FIG. 1 is in the mandatory mode, the controller cycles the motor or solenoid 1 for 1.5 seconds and off for 3.5 seconds. During the 1.5 second period the motor is on, the air flow rate starts at 600 cc/second and decreases to 200 cc/second. This is done to minimize the peak pressure in the victim's airway, thus reducing the chance of gastric insufflation. This delivery pattern results in 12 breaths per minute being delivered and is therefore consistent with recommendations made by the American Heart Association. specifically, the American Heart Association guideline for cardiopulmonary resuscitation calls for the delivery of chest compressions at a rate of 80 per minute and one breath every five compressions. Of course, other protocols in terms of breaths per minute and chest compressions per minute could be provided through minor changes to the program or inputs to the controller. Triggering of the cadence control switch 22 causes the controller 20 to send timing signals to the speaker 26 which the user hears and uses to synchronize the delivery of chest compressions.

Specifically, whenever the apparatus enters the mandatory mode, two initial breaths are delivered to the victim. The user then receives a voice instruction to check the victim's pulse and to turn the cadence control switch 22 to the "on" position if there is no pulse. The apparatus then delivers breaths and timed voice instructions to "press" as indicated above. This not only, assures consistent compressions, but allows the device to deliver a breath between compressions. The microprocessor of the controller 20 monitors the pressure sensor 12 between each breath delivered by the device to detect inspiratory effort by the victim. If such effort is detected, the device automatically switched to the spontaneous mode.

Turning to the embodiment shown in FIG. 2, the gas source 30 will typically be a high pressure oxygen cylinder. The regulator 32 maintains the gas pressure at a predetermined value so that flow through solenoid valves (the $O_2$ delivery valve 34 and the exhalation valve 14) can be predicted.

The exhalation valve 14 is required to vent the tubing at the end of the breath so that the victim can exhale through the non-rebreathing valve 16. The delivery valve 34 delivers gas from the regulator 32 to the victim. The delivery valve 34 can be a proportional type valve which allows for adjustment of the flow rate by varying the current applied by the control circuit 20. Alternatively, valve 34 can be a digital type which has only an "on" position and an "off" position.

The sensor 12 delivers an analog signal proportional to pressure to an analog-to-digital converter which is part of the control circuit. The microprocessor "reads" the analog-to-digital converter to monitor victim pressure. The sensor 12 may be a piezoresistive type such as a resistive bridge with approximately a 30–50 millivolt output. Only inspiratory pressure is monitored because the victim exhales through the non-rebreathing valve 16. In this configuration, the controller 20 uses the signal from sensor 12 to perform three functions. First, it ensures that there is no over pressurization during inspiration. Second, it senses inspiratory effort or spontaneous breathing on the part of the victim. The controller 20 can use the sensed back pressure to determine whether there is a leak, whether the face mask has been displaced, or whether there is an obstruction between the gas source and face mask.

In response to the switch settings and signals received from the sensor 12, the microprocessor of the controller 20 automatically operates the apparatus. It controls the valves 14 and 34. In addition to a microprocessor and analog-to-digital converter, the control circuit includes MOSFET drivers for the valves with "flyback" diodes in parallel, a voice prompt module for driving the speaker 26, and an amplifier circuit coupled with the pressure sensor 12.

Now that the apparatus of two separate embodiments of the invention have been described, use and operation of the invention will be discussed. Operation of the invention is based upon two sets of inputs and two sets of outputs. First, the apparatus has various switches. Some of these switches are digital in that the user is selecting between an "on" or "off" position. The example of such a switch is the cadence control switch 22 shown in FIG. 1. Some of these switches may be analog. For example, one or more potentiometers 36 can be provided to provide the controller 20 with an indication of the patient's size, age, or other pertinent information. When potentiometers such as 36 are used, it is necessary to couple them to the control circuit via an A/D converter in the control circuit 20. Still another switch might be a read switch coupled to the base and cover of the housing which contains the apparatus. Lifting the cover can serve to actuate such a switch which activates the apparatus. Other than the switches such as 22 and 36, a second set of analog inputs is supplied by the amplified pressure sensor 12. Again, this sensor 12 is electrically coupled to the converter so that the microprocessor of the controller 20 can read the information in a digital form.

The three outputs provided by the apparatus include a signal sent to the actuator of the delivery valve 34. This signal can be a pulse width modulated signal, the duty cycle of which is set at a predetermined value. A second signal is sent to the actuator of the exhalation valve 14 which vents pressure from the tubing. Finally, digital signals are sent from the microprocessor to the voice prompt module. These signals include an address and an enable signal to identify the message that should be audibly generated via the speaker 26.

When the apparatus is turned on, it immediately calibrates the pressure sensor 12 to indicate a zero reading. The controller 20 also immediately sends a signal to the voice prompt module which instructs the module to provide, for example, the following message over the speaker: "Call 9-1-1, turn cylinder knob "on", select patient size on knob, assure that there is no vomit or obstruction in mouth, place mask on face, point over the nose, tilt head back, pull jaw forward". Next, the apparatus reads the patient's size setting on the potentiometer 36 and calculates parameters related to the inspiratory and expiratory phases. These parameters include inspiratory time, expiratory time, maximum flow, maximum pressure, spontaneous breath pressure threshold and minimum pressure expected. Entering the expiratory subroutine, the controller 20 begins by setting the timer to zero and turning on the expiratory valve. When the timer times out, the expiratory valve is turned off. A voice prompt is then delivered one-half second before onset of the inspiratory subroutine. This voice prompt delivers the message "ventilating, do not compress chest" via the speaker.

In the inspiratory subroutine, the timer is again set to zero. A check of pressure is then made. If the pressure is over the maximum, the flow rate is reduced. Also, an optional voice prompt may be delivered warning of high pressure. The controller 20 also calculates flow and again senses pressure. This time, if pressure is too low, a voice prompt is issued stating "There is either a massive leak, the oxygen is not turned on, or the mask is not on the victim's face". Once the timer times out, the apparatus returns to the main loop.

While in the main loop, the apparatus decides if it should be in the spontaneous mode. If so, flow, inspired volume and pressure are all monitored. If there is no inspiratory effort reflected in a change in pressure, then the apparatus loops back to the mandatory mode.

An important aspect of the present invention is the way the apparatus delivers flow in a decelerating wave form. Given this wave form, flow rate decreases during the breath either linearly or otherwise. In the apparatus shown in FIG. 2, this is accomplished through the utilization of the microprocessor and a delivery valve 34 actuated by a proportional solenoid. The microprocessor can vary the opening of the valve during the breath based upon signals sent to the solenoid. Another way is to use a digital on-off solenoid to actuate valve 34, and to use pulse width modulation to vary the flow rate during the breath. When a digital solenoid is used, the valve 34 is turned on and off at a rapid rate. The valve 34 is initially turned on for a greater percent of the total time and the open percent (duty cycle) is decreased during the breath. This is advantageous in that it minimizes the pressure required to deliver a given tidal volume. Thus, back pressure due to restrictions in the lung is minimized late in the breath by reducing the flow rate. This is significant because late in the breath, back pressure due to compliance is maximum. Minimizing pressure is important because this reduces the chance of gastric insufflation, which is a major cause of vomiting. Aspiration of vomited materials can cause serious lung trauma. A higher peak flow may prove acceptable because the wave form is decelerating.

What is claimed is:

1. For use in a rescue in assisting a victim in an emergency situation, a portable breathing assist apparatus comprising:
   (a) a source of pressurized gas;
   (b) a face mask;
   (c) tubing creating a fluid flow path between said source of pressurized gas and said face mask;
   (d) means for sensing the pressure of gas within said tubing;
   (e) a non-rebreathing valve which directs gas through the face mask into a victim upon inhalation and out to the atmosphere upon exhalation;
   (f) an exhalation valve coupled to an exhalation valve actuator for venting gas from said tubing to the atmosphere when said exhalation valve is open;
   (g) actuator means for regulating the delivery of pressurized gas from said source of pressurized gas;
   (h) a controller coupled to said means for sensing pressure, said exhalation valve actuator, and said actuator means, said controller including a voice module coupled to a speaker for issuing voice instructions to a rescuer via the speaker.

2. The apparatus of claim 1 wherein said source of pressurized gas is a pump and said actuator means for regulating the release of the pressurized gas is a motor.

3. The apparatus of claim 2 wherein said controller controls when the motor is on, when the motor is off, and the speed of the motor.

4. The apparatus of claim 3 wherein the controller cycles the motor so that it is on for a first predetermined period of time period followed by a second predetermined period of time when the motor is off.

5. The apparatus of claim 4 wherein said controller varies the speed of the motor during said first period so that the flow of gas from said source of pressurized gas is initially at a first rate and decreases to a second rate.

6. The apparatus of claim 1 wherein said source of pressurized gas is a gas tank and said actuator means for regulating the release of the pressurized gas is a release valve coupled to a solenoid.

7. The apparatus of claim 6 wherein said solenoid is a proportional solenoid capable of varying the size of the opening of said release valve.

8. The apparatus of claim 7 wherein said proportional solenoid is responsive to signals received from the controller to open, close, or alter the size of the opening of the release valve.

9. The apparatus of claim 8 when said controller sends signals to the proportional solenoid causing the proportional solenoid to cycle the release valve so that it is open for a first predetermined period of time followed by a second predetermined period of time when the release valve is closed.

10. The apparatus of claim 9 wherein said controller sends signals to the proportional solenoid during said first predetermined period of time so that the flow of gas from said source of pressurized gas is initially at a first rate and decreases to a second rate.

11. The apparatus of claim 6 wherein said solenoid is a digital solenoid.

12. The apparatus of claim 11 wherein said digital solenoid is responsive to signals received from the controller to open and close the release valve.

13. The apparatus of claim 12 wherein said controller sends modulated signals to the digital solenoid.

14. The apparatus of claim 12 wherein said controller sends signals to the digital solenoid causing the digital solenoid to cycle the release valve open and closed for a first predetermined period of time followed by a second predetermined period of time in which the release valve is closed.

15. The apparatus of claim 14 wherein during said first predetermined period of time, the modulated signals sent by the controller to the digital solenoid cause the gas to flow from the source of pressurized gas past the release valve initially at a first rate and then at a lower rate.

16. The apparatus of claim 1 further including setting means coupled to said controller.

17. The apparatus of claim 16 wherein said setting means includes a switch which is actuatable by a rescuer to send a signal to the controller which causes the controller to issue a cadence via the speaker to be used by a rescuer in applying chest compressions to a victim as part of the administration of cardiopulmonary resuscitation.

18. The apparatus of claim 16 wherein said setting means includes a potentiometer which is actuatable by a rescuer to send a signal to the controller representative of a characteristic of a victim being administered to.

19. The apparatus of claim 16 wherein said controller controls the operation of the exhalation valve actuator and the actuator means in accordance to a pre-programmed set of instructions in response to inputs received by said controller from said means for sensing pressure.

20. The apparatus of claim 19 wherein said controller controls the operation of the exhalation valve actuator and the actuator means also in response to inputs received from said setting means.

21. The apparatus of claim 1 wherein said apparatus has a start-up mode in which a plurality of voice instructions are delivered via the speaker to a rescuer.

22. The apparatus of claim 21 wherein, when the apparatus is in said start-up mode the controller monitors signals received from the means for sensing pressure to determine whether a victim is making inspiratory effort based upon changes in the signals received from the means for sensing pressure.

23. The apparatus of claim 1 wherein said apparatus has a spontaneous mode of operation in which the controller (a) determines the volume of gas inhaled during each inhalation by a victim based upon changes in signals received from the means for sensing pressure; (b) sends signals to the actuator means to increase the flow of gas to the face mask if the inhaled volume of gas is below a predetermined level; and (c) monitors the time between inhalations by a victim.

24. The apparatus of claim 1 wherein said apparatus has a mandatory mode of operation in which the controller sends signals to the actuator means causing gas to flow from the source of pressurized gas to the face mask for a first predetermined period of time and restricting the flow of gas from the source of pressurized gas to the face mask for a second predetermined period of time.

25. The apparatus of claim 24 wherein during said first predetermined period of time the flow of gas is at a first rate and then decreases to a second rate.

26. The apparatus of claim 1 wherein said source of pressurized gas is a pump and said actuator means for regulating the release of pressurized gas is an electromagnetic solenoid that drives said pump.

27. The apparatus of claim 26 wherein said controller controls when the electromagnetic solenoid is on, when the electromagnetic solenoid is off, and the speed of the electromagnetic solenoid.

28. The apparatus of claim 1 wherein said controller responds to signals from pressure transducer to indicate a leak, displacement of mask or obstruction in the flow of pressurized gas from the source to the face mask.

* * * * *